United States Patent [19]

Heil, Jr. et al.

[11] Patent Number: 4,819,662
[45] Date of Patent: Apr. 11, 1989

[54] CARDIAC ELECTRODE WITH DRUG DELIVERY CAPABILITIES

[75] Inventors: Ronald W. Heil, Jr., Roseville; Robert C. Owens, Forest Lake; Brian D. Pederson, St. Paul, all of Minn.

[73] Assignee: Cardiac Pacemakers, Inc., St. Paul, Minn.

[21] Appl. No.: 112,518

[22] Filed: Oct. 26, 1987

[51] Int. Cl.$^4$ .............................................. A61N 1/00
[52] U.S. Cl. .................. 128/786; 128/419 P
[58] Field of Search .......................... 604/20, 891–892; 128/786, 784, 419 P

[56] References Cited

U.S. PATENT DOCUMENTS

| 4,360,031 | 11/1982 | White | 128/786 |
| 4,418,704 | 12/1983 | Theisen et al. | |
| 4,506,680 | 3/1985 | Stokes | 128/786 |
| 4,577,642 | 3/1986 | Stokes | 128/786 |
| 4,606,118 | 7/1986 | Cannon et al. | |
| 4,711,251 | 12/1987 | Stokes | 128/786 |

Primary Examiner—Francis Jaworski
Assistant Examiner—George Manuel
Attorney, Agent, or Firm—Orrin M. Haugen; Thomas J. Nikolai; Frederick W. Niebuhr

[57] ABSTRACT

An implantable cardiac pacing lead includes a porous, platinum electrode, a flexible electrically conductive coil, and a crimp tube coupling the electrode to the distal end of the coil. A recess in the crimp tube, open to the electrode at the crimp tube distal end, houses a matrix impregnated with a therapeutic drug. The electrode is highly porous and loaded with a therapeutic drug in liquid or solid form. Immediately upon implant of the electrode at a selected myocardial location, the electrode begins dispensing the therapeutic drug. Meanwhile, the matrix begins to elute its drug at a rate more suited to chronic treatment. If desired, the recess can extend through the crimp tube to permit proximal end loading of the drug carrying matrix. A silicone plug, or an additional and proximal crimp tube section, is inserted into the recess after loading of the matrix to provide the required fluid seal. Finally, a variety of different matrices can be housed in the recess, to provide elution of different drugs and at differing rates.

25 Claims, 2 Drawing Sheets

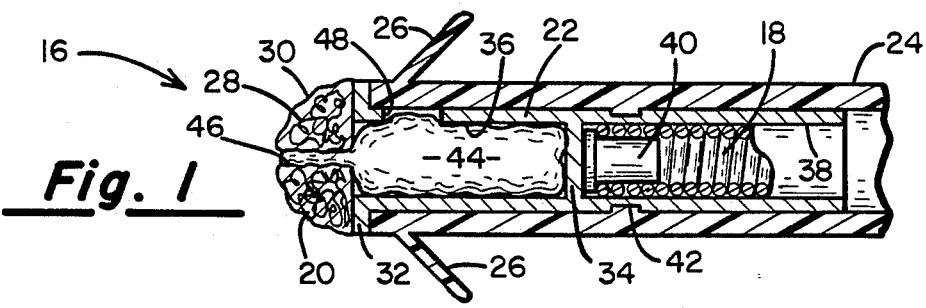
_Fig. 1_
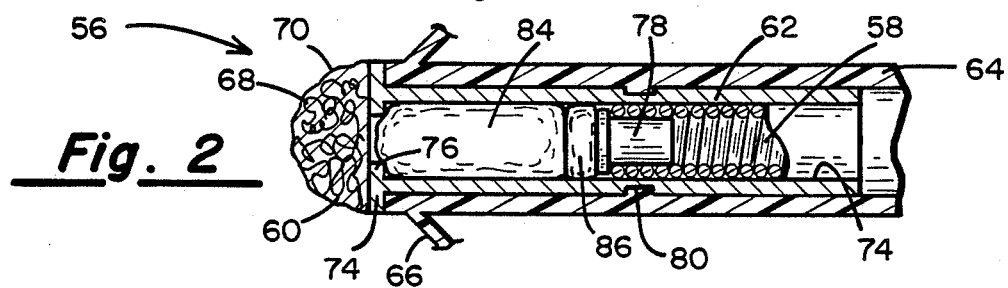
_Fig. 2_
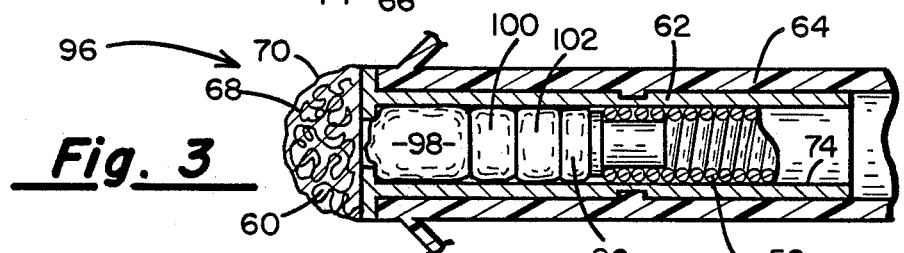
_Fig. 3_
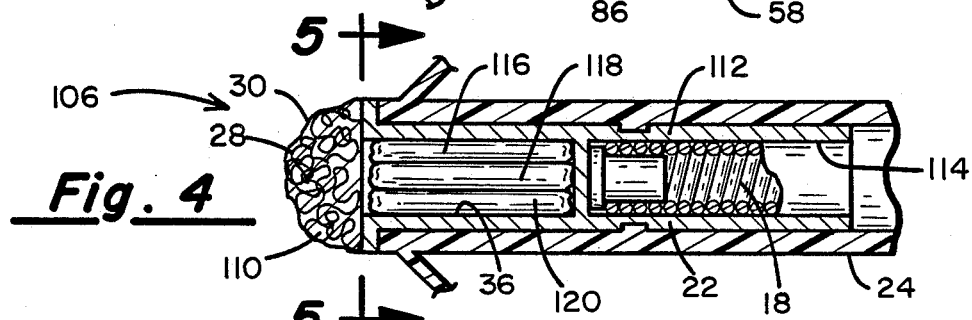
_Fig. 4_
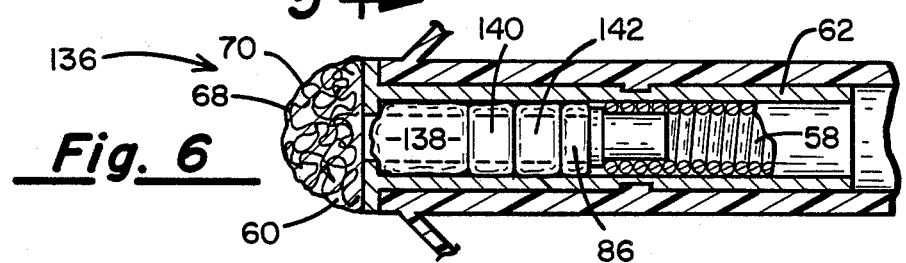
_Fig. 6_
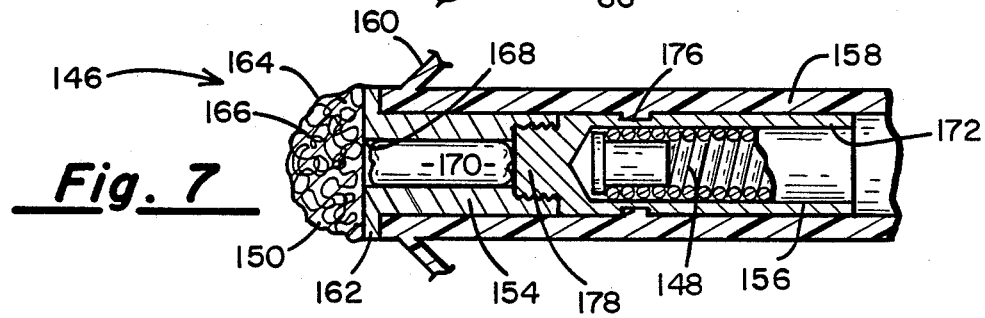
_Fig. 7_

CARDIAC ELECTRODE WITH DRUG DELIVERY CAPABILITIES

BACKGROUND OF THE INVENTION

This invention relates to implantable diagnostic and chronic therapeutic leads, and more particularly to cardiac pacing leads capable of delivering drugs near the point of implant.

Cardiac pacing leads are recognized as well suited for carrying pulse stimulation signals to the heart from a pacemaker, and for monitoring heart electrical activity from outside the body. Typically, such leads are sufficiently flexible and small in diameter for intravenous introduction to a cardiac cavity, whereupon an electrode at the distal end of the lead is implanted into the endocardium to secure the lead. A persistent problem accompanying the use of pacemaker leads is the increase in stimulation threshold, both acute and chronic, caused by the interaction between the electrode and body tissue at the point of implant. Approaches to reducing the threshold, or conversely to increase the lead sensitivity, include introduction of thin, limp leads, small porous electrodes, electrodes with activated surfaces, and electrodes of "biocompatible" materials such as carbon.

Relatively recent among these approaches is a local introduction of a drug for reducing the stimulation threshold. For example, U.S. Pat. No. 4,506,680 (Stokes) shows a body implantable lead with a silicone rubber plug housed in a cavity within the lead and impregnated with dexamethasone sodium phosphate. An elution bore is filled with sintered metal microparticles in order to control the rate of drug elution through the use of this densely packed medium. A sealing washer, backed by a metal disc, separates the distal and proximal cavities in the crimp tube, with the drug plug in the distal cavity. U.S. Pat. No. 4,557,642 (Stokes) shows a crimp tube having a medial wall to form in the crimp tube a distal cavity to house a drug matrix, mainly a powdered form of molecular sieve material. Side apertures are provided in the crimp tube for loading the drug. These devices, while suitable for certain applications, fail to address the need for rapid drug delivery to counter acute threshold increase, for selectively combining drugs for either sequential or simultaneous local delivery, or for convenient loading of a drug delivery matrix into a lead.

Therefore, it is an object of the present invention to provide an implantable cardiac pacing lead adapted for rapid drug delivery immediately upon implant to counter an acute stimulation threshold increase.

Another object is to provide a cardiac pacing lead having a porous electrode capable of holding a drug in liquid form or solid form for acute local delivery upon implant, in combination with a drug impregnated matrix for chronic drug delivery.

Another object of the invention is to provide a pacemaking led employing a plurality of drug matrices for selectively varying the type of drug, concentration of drug and drug delivery rate.

Yet another object is to provide a body implantable lead enabling convenient, proximal end loading of one or more drug impregnated matrices into structure coupling the lead electrode with the distal end of the lead conductor.

SUMMARY OF THE INVENTION

To achieve these objects, there is provided an intravascular lead implantable inside a patient. The lead includes a porous, electrically conductive electrode, and a flexible electrical conductor. A flexible, biocompatible and dielectric sheath surrounds the conductor along substantially its entire length. A coupling means electrically and mechanically joins the electrode with respect to the distal end of the conductor. The electrode is joined to and substantially covers the distal end of the coupling means. A recess is formed in the coupling means and is open to the electrode. A matrix containing a therapeutic drug is retained in the recess. The electrode is loaded with a therapeutic drug in liquid form or solid form, and is positionable for fixation to body tissue at a selected location. The electrode is sufficiently porous to freely dispense the drug in liquid or solid form at the selected location upon contact with bodily fluids, and also to facilitate the dispensing of the drug from the matrix to the selected location.

To facilitate loading of the drug matrix into the recess, a bore can be formed through the electrode from the recess to the lead exterior. Alternatively, the recess can extend through the coupling means to its proximal end, to permit a proximal insertion of the matrix into the recess. A plug is then inserted into the coupling means and provides a substantially fluid-tight seal between the matrix and conductor.

Preferably the electrode has a high porosity, at least seventy-five percent porous by volume. This ensures that the electrode does not substantially hinder fluid flow, for a rapid delivery of a therapeutic drug from the electrode to the desired location of implant. Consequently, a rapid, local drug delivery is provided, to reduce the problem of acute stimulation threshold increase. The lead porosity counters chronic threshold increase as well, in that it allows substantially free fluid flow into and out of the recess, maintaining long term delivery of drug from the matrix. Additionally, high porosity encourages lead fixation to the cardiac tissue for stable, long term lead performance.

Another aspect of the present invention is an intravascular, implantable lead including an electrode positionable for fixation to bodily tissue at a selected location, and a flexible electrical conductor. A flexible, biocompatible and dielectric sheath surrounds the conductor along substantially its entire length. A first coupling means electrically and mechanically joins the electrode with respect to the conductor distal end. A recess is formed in the first coupling means and open to its proximal end, to permit proximal insertion of a drug carrying matrix into the coupling means. A sealing means is provided for connection with the first coupling means following the insertion of the matrix. The sealing means forms a substantially fluid-tight seal between the matrix and the conductor. A fluid passageway is provided for movement of bodily fluid into and out of the recess.

In one embodiment of the invention, the recess is cylindrical and the sealing means is an elastically deformable cylindrical plug having an outside diameter slightly larger than the inside diameter of the recess. As an alternative, the sealing means can be a second coupling means between the first coupling means and the conductor. The distal end of the second coupling means is configured for engagement with the proximal end of the first coupling means. Either approach enables convenient, proximal loading of the drug impregnated matrix.

Yet another aspect of the invention is an intravascular, implantable lead including an electrode positionable for fixation to bodily tissue at a selected location, and a flexible electrical conductor. A flexible, biocompatible and dielectric sheath surrounds the conductor substantially along its entire length. A coupling means electrically and mechanically joins the electrode and distal end of the conductor. A recess is formed in the coupling means, and a passageway admits bodily fluid into and out of the recess. A plurality of matrices are contained in the recess, each loaded with a therapeutic drug. The matrices differ from one another in at least one of the following respects:
  (a) the drug contained in the matrix;
  (b) the concentration of the drug contained in the matrix; and
  (c) the constituent material forming the matrix.

A prominent feature of this invention is that it enables a selective delivery of different drugs, either simultaneously or consecutively. Or, the same drug, provided in a concentration increasing sequentially in the matrices from the most proximal to the most distal, enables a stepped decrease in the rate of delivery. Varying the matrix constituent can have a similar effect.

Thus, pacemaking leads constructed in accordance with the present invention substantially increase the versatility of local rug delivery, in terms of drug delivery rates, kinds of drugs delivered, and simultaneous versus serial delivery. The highly porous electrode can be loaded with a therapeutic drug in liquid or solid form for immediate delivery to the treatment site, and further does not restrict later drug elution from a drug impregnated matrix.

IN THE DRAWINGS

For a better appreciation of these and other features and advantages, reference is made to the detailed description of the preferred embodiments along with the drawings, in which:

FIG. 1 is a side sectional view of a cardiac pacing lead constructed in accordance with the present invention;

FIG. 2 is a side sectional view of the distal end portion of a second embodiment cardiac pacing lead;

FIG. 3 is a side sectional view of a third embodiment cardiac pacing lead;

FIG. 4 is a similar sectional view of a fourth embodiment cardiac pacing lead;

FIG. 6 is a side sectional view of the distal end region of a fifth embodiment cardiac pacing lead;

FIG. 7 is a similar sectional view of a sixth embodiment cardiac pacing lead.

DETAILED DESCRIPTION OF THE PREFERRED EMBODIMENTS

Figure 5:
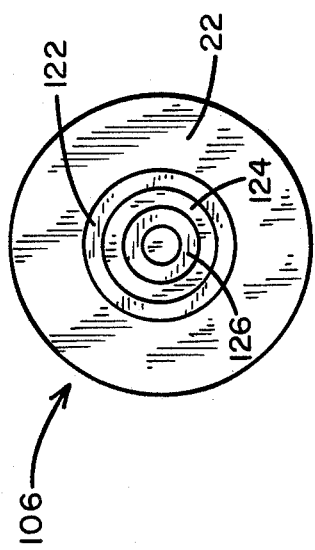
FIG. 5 is a sectional view taken along the line 5—5 in FIG. 4, showing the pacing lead in FIG. 4 but with an alternative drug carrying matrix.

Turning now to the drawings, there is shown in FIG. 1 the distal end region of an implantable cardiac pacing lead 16. Devices such as lead 16 typically are inserted intravenously, for example into the subclavian vein or the cephalic vein, and progressively moved toward the heart until the distal end reaches a selected cardiac chamber. With the distal tip positioned at a selected location, the lead proximal end, still outside the body, is maneuvered to implant the distal tip into the endocardium. The implanted lead transmits electrical signals between the selected location in the heart and the lead proximal end, for one or both of two purposes: (a) to monitor heart electrical activity at the selected location; and (b) to carry stimulating signals to the selected location from a pulse generator (not shown) connected to the lead proximal end.

To transmit the electrical signals there is provided an electrical conductor, shown in FIG. 1 as a single wound coil 18 formed of a nickel alloy. The coil provides maximum flexibility for conforming to the vein, with minimal stress on the conductor. At the distal end of the lead is an electrode 20, electrically and mechanically coupled to coil 18 by a platinum alloy crimp tube 22. A flexible, dielectric sheath 24 surrounds the coil and crimp tube. The sheath is formed of a biocompatible material such as silicone rubber. A plurality of tines 26 are formed as part of sheath 24 near its distal end, and are employed to secure the lead distal end to the selected myocardial location.

Electrode 20 is constructed of a platinum alloy, stretched to a thin wire 28, then crumpled and packed against the distal end of crimp tube 22. A platinum alloy screen 30, fastened to the periphery of the crimp tube distal end, maintains the crumpled platinum alloy wire in place. So constructed, electrode 20 is highly porous, for example consisting of approximately twenty percent platinum alloy by volume, the remaining eighty percent being open to receive a therapeutic drug in liquid or solid form, or to permit passage of bodily fluids through electrode 20.

Crimp tube 22 is elongate and cylindrical, with a radially outward flange 32 at its distal end to serve as an abutment for sheath 24 and an anchor for screen 30. A medial wall 34 isolates a distal recess 36 of the crimp tube from a proximal recess 38. The distal end of conductor coil 18 is retained in proximal recess 38 by a core pin 40 and a crimp 42 in the crimp tube wall, just proximally of a radially enlarged head portion of the core pin.

A drug loaded matrix 44, e.g. a biocompatible silicone adhesive compound impregnated with dexamethasone sodium phosphate or other desired therapeutic drug, is loaded into distal cavity 36 and retained within the cavity by electrode 20. Matrix 44, while pliable and prior to curing, is loaded manually into the assembled lead. Loading can occur through a bore 46 formed through electrode 20 between the distal recess and the lead exterior. In the event of such distal loading, a portion of the drug matrix 44 remains in bore 46 as illustrated. Alternatively, a load slot 48 is provided through crimp tube 22 along its side and near its distal end. Slot 48 provides a larger opening for loading the matrix, and is particularly useful when the matrix has a high viscosity rendering distal loading difficult or impossible. While lead 16 in FIG. 1 is shown having both bore 46 and load slot 48, it can be appreciated that typically either of these alone would suffice. A drug loaded matrix in uncured or powdered form could be accommodated, as well, by either the bore or slot. Loading an uncured, pliable matrix provides substantially perfect conformation of the resulting cured matrix to any recess shape incorporated, for example a recess having an enlarged proximal diameter, holding the final cured matrix in place. Additionally, any potential adhesive characteristics of the matrix can provide bonding to the recess wall.

It is not always convenient to load a drug impregnated matrix, uncured, into a crimp tube recess. Accordingly, FIG. 2 illustrates a second embodiment lead 56 which permits the use of a matrix consisting of a previously formed, solid plug. An electrically conductive coil 58 and porous electrode 60 are mechanically and electrically connected by a crimp tube 62. A sheath 64, provided with tines 66, surrounds the crimp tube and conductive coil. Electrode 60 is constructed of crumpled and packed platinum alloy wire 68, maintained against the distal end surface of crimp tube 62 by a screen 70 fastened to the crimp tube at a radially outwardly extended flange 72.

A cylindrical recess 74 is formed in crimp tube 62, open to the proximal end of the crimp tube and spanning substantially the length of the tube. A radially inward extension 76 of the crimp tube at its distal end forms a reduced diameter neck in the recess. A core pin 78 and the distal end of coil 58 are fastened in recess 74 by a crimp 80.

Prior to the fastening of coil 58, a preformed, solid drug impregnated matrix 84 is inserted into recess 74 at the proximal end of crimp tube 62, and positioned near the crimp tube distal end as shown. Following matrix insertion, a silicone rubber plug 86, cylindrical and with a slightly larger diameter than the interior diameter of the crimp tube, is inserted to a position proximally of matrix 84. Plug 86 forms a substantially moisture-tight seal between the distal portion of recess 74 and the proximal portion of the recess.

The proximal loading feature of lead 56 permits the use of pre-manufactured, solid drug matrices. This eliminates the need for preparing the drug matrix during lead assembly, reducing manufacturing costs in that the assemblers of such leads need not be skilled in determining the proper combination of drugs and matrix constituents, or in mixing these elements to create the matrix.

FIG. 3 illustrates a third embodiment lead 96 similar in construction to lead 56 in FIG. 2, with similar parts indicated by the same numerals. The major difference between leads 56 and 96 is in the provision of three solid, preformed drug matrices 98, 100 and 102 in lieu of a single matrix. This arrangement results in an essentially consecutive elution process, whereby elution is substantially complete in each particular matrix before it begins in the next proximal matrix. Consequently, the matrices can be impregnated with the same drug, but in progressively decreasing concentration sequentially from the most distal matrix 98 to proximal matrix 102. The size of each matrix relative to the others may as well be selectively varied, to permit a stepped elution involving selected elution rates and for selected durations. Alternatively, the elution rate may be varied by constructing the matrices of different constituents.

FIG. 4 shows an inside view of a fourth embodiment facing lead 106 similar in construction to lead 16 in FIG. 1, with like parts given like numerals. Electrode 110 includes a crumpled platinum alloy wire 28 contained by a screen 30, but in contrast to lead 20 includes no bore. Also, no load slot is formed in crimp tube 112. Rather, a bundle of elongate and cylindrical preformed and solid drug matrices are loaded into distal recess 114 prior to fastening of electrode 110 to the crimp tube. Three of these matrices are shown at 116, 118 and 120.

The bundle of parallel matrices enables a simultaneous or concurrent elution of drugs from all of the matrices. As an example, matrix 116 can be impregnated with an anti-inflammatory drug, matrix 118 with an anti-arrhythmic drug, and matrix 10 with an antibiotic. A bundle of numerous matrices, of course, affords flexibility in determining the proportion of various drugs selected, permitting the tailoring of treatment to individual patients without the need to create custom matrix constituent and drug mixtures.

FIG. 5 is a forward sectional view of lead 106 of FIG. 4, but showing the lead loaded with a series of toroidal, concentric matrices 122, 124 and 126. This arrangement results in simultaneous elution and therefore affords the advantages discussed in connection with FIG. 4. Furthermore, the toroidal configuration provides a convenient means for close packing of drug matrices of different sizes.

FIG. 6 shows a fifth embodiment pacing lead 136 similar in construction to the leads in FIGS. 2 and 3, with like parts given like numerals. The principal difference is that recess 74 of crimp tube 62 contains three sequentially arranged toroidal drug impregnated matrices 138, 140 and 142. This arrangement of matrices combines characteristics of sequential and simultaneous elution configurations, although elution perhaps is more similar to simultaneous elution. Furthermore, the arrangement takes advantage of the greater matrix surface exposure, and therefore more rapid elution, of the toroidal matrix.

If the matrices are sufficiently small in outside diameter (relative to recess 74) so that their inside and outside surfaces are exposed to bodily fluids, the internal surface area of each matrix is enlarged, while the external surface is reduced, in the course of drug elution. As these changes in surface area substantially offset one another, the drug elution rate is constant.

Alternatively, if an increasing rate of drug elution is desired, the matrices are provided with an outside diameter substantially equal to the inside diameter of the recess, to expose essentially only their internal surfaces. Then, as drug elution proceeds, the exposed internal surface area available for drug elution increases. This feature of the toroidal structure results in a rate of drug delivery which increases with time, assuming a uniform distribution of the drug throughout the matrix. In this manner, drug delivery can be selectively and gradually accelerated.

FIG. 7 illustrates a sixth embodiment pacing lead 146 including a conductive coil 148 and porous electrode 150 connected to one another by a crimp tube assembly 152, consisting of a distal crimp tube section 154 and a proximal section 156. A dielectric sheath 158 including tines 160 surrounds the crimp tube assembly and conductive coil.

Distal crimp tube section 154 includes a radially outwardly directed flange 162 for abutment by sheath 158 and for supporting a screen 164 which maintains crumpled platinum alloy wire 166 in its hemispherical configuration against the crimp tube distal end. A recess 168 is formed through crimp tube section 154, open to electrode 150 and also permitting the loading of a preformed, solid drug impregnated matrix 170 into recess 168 at the proximal end of crimp tube section 154. Recess 168 is widened near the proximal end of section 154, and internally threaded.

A recess 172 is formed in proximal crimp tube section 156, for containment of conductive coil 148 and core pin 174, and is crimped near the core pin as shown at 176. Crimp tube section 156 includes a distal extension 178 externally threaded for engagement with distal section 154.

Crimp tube sections 154 and 156, when separated, permit proximal loading of matrix 170. When threaded together as shown in FIG. 7, these sections form a crimp tube assembly that prevents fluid flow between recesses 168 and 172.

All of the above-described leads are provided with a highly porous electrode as described in connection with lead 16, and thus are particularly well suited for drug elution, whether from a matrix or directly from the electrode. First, when used in connection with a drug impregnated matrix as described, the electrode permits bodily fluids to flow substantially freely into and out of the matrix containing recess. Consequently, while the electrode may maintain the matrix or matrices within the recess, it does not materially hamper elution.

Secondly, due to its high porosity, the electrode is well suited for loading with a therapeutic drug in liquid or solid form. The result, particularly as compared to utilizing a drug impregnated matrix alone, is a much more rapid and direct delivery of drug to the location of implant.

Figure 8:
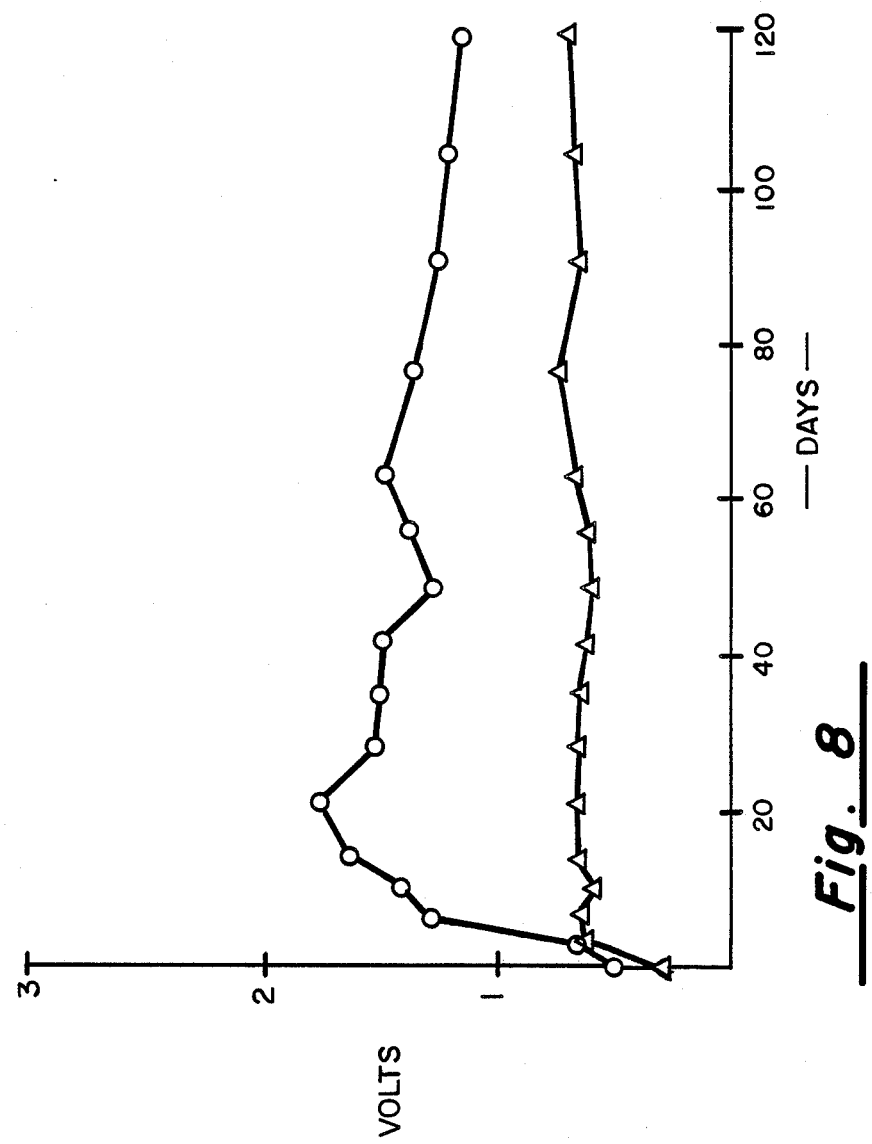
FIG. 8 is a graph illustrating the utility of a drug loaded porous electrode in reducing the acute and chronic stimulation threshold.

The graph in FIG. 8 illustrates the beneficial result of loading a porous electrode with a steroid. The upper curve, representing a non-loaded control electrode, illustrates an early peak in stimulation threshold of approximately 1.8 volts, followed by a chronic threshold of about 1.3 volts. By comparison, the steroid loaded electrode does not exhibit an acute peak in stimulation threshold levels, and maintains a relatively stable chronic threshold level of approximately 0.7 volts.

In addition to the general reduction in stimulation thresholds, the removal of the early stimulation threshold peak is itself a substantial advantage. This eliminates the need to provide a pacing apparatus with a chronic voltage level set high enough to overcome the initial peak, or alternatively to attempt to program an early voltage peak into the pacing regimen, hopefully matching the actual peak in stimulation threshold. Thus, in accordance with the present invention, the porous electrode may be loaded with primarily an anti-inflammation drug to reduce or eliminate an acute peak in stimulation threshold level, while an accompanying matrix or matrices can be tailored to chronic treatment.

Thus, a cardiac pacing lead constructed in accordance with the present invention permits a selection from among various drugs, drug concentrations and drug elution rates, for sequential or simultaneous administration, tailored to the needs of a particular patient. A silicone plug or two-part crimp tube assembly affords the advantage of proximal loading, enabling the use of preformed, solid drug impregnated matrices.

What is claimed is:

1. An intravascular lead implantable inside a patient, including:
an electrically conductive electrode having a porosity of at least seventy-five percent; a flexible electrical conductor; a flexible, biocompatible and dielectric sheath surrounding said conductor along substantially the entire length thereof; a coupling means for electrically and mechanically joining said electrode with respect to the distal end of said conductor, said electrode joined to and substantially covering the distal end of said coupling means; means forming a recess in said coupling means and open to said electrode; and a matrix containing a water soluble drug and retained in said recess; and
wherein said electrode is loaded with a therapeutic drug, and is positionable for fixation to body tissue at a selected location, said electrode being sufficiently porous to freely dispense said drug at said selected location upon contact with bodily fluid, and further sufficiently porous to facilitate dispensing of the drug from said matrix to said selected location.

2. The intravascular lead of claim 1 further including:
means forming a bore through said electrode from said recess to the exterior of said electrode to permit loading of said matrix into said recess through said bore.

3. The intravascular lead of claim 2 wherein:
said bore houses a portion of said matrix after said loading.

4. The intravascular lead of claim 1 including:
means forming a slot in said coupling means for the loading of said matrix into said recess.

5. The intravascular lead of claim 1 wherein:
said recess extends through said coupling means to the proximal end thereof, thereby to permit insertion of said matrix into said recess from the proximal end of said coupling means.

6. The intravascular lead of claim 5 further including:
a plug insertable into said coupling means at the proximal end thereof following insertion of said matrix, for forming a substantially fluid-tight seal between said matrix and said conductor.

7. The intravascular lead of claim 1 wherein:
said electrode is fastened to said coupling means at the periphery of the coupling means distal end, thereby to retain said matrix in said recess.

8. The intravascular lead of claim 1 wherein:
said recess is cylindrical, said matrix is cylindrical and has an outside diameter substantially equal to the inside diameter of said recess, and said coupling means includes an annular, radially inwardly directed flange at its distal end to retain said matrix in said recess.

9. An intravascular, implantable lead comprising:
an electrode positionable for fixation to bodily tissue at a selected location; a flexible electrical conductor; a flexible, biocompatible, dielectric sheath surrounding said conductor along substantially the entire length thereof; a first coupling means for electrically and mechanically joining said electrode with respect to the distal end of said conductor; and
means forming a recess in said first coupling means and open to the proximal end of said first coupling means to permit proximal insertion of a drug carrying matrix into said coupling means; and
a sealing means for connection with said first coupling means following said proximal insertion of said matrix, for forming a substantially fluid-tight seal between said matrix and said conductor; and means forming a fluid passageway for movement of bodily fluid into and out of said recess distally of said sealing means.

10. The intravascular lead of claim 9 wherein:
said recess is cylindrical, and said sealing means comprises an elastically deformable cylindrical plug having an outside diameter slightly larger than the inside diameter of said recess.

11. The intravascular lead of claim 10 wherein:
said plug is constructed of silicone rubber and fastened to the interior of said recess with a biocompatible adhesive.

12. The intravascular lead of claim 9 wherein:
said sealing means comprises a second coupling means between said first coupling means and said conductor, the distal end of said second coupling means being configured for engagement with the proximal end of said first coupling means.

13. The intravascular lead of claim 12 wherein:
said second coupling means includes a reduced diameter portion at its distal end, of a size to enter said recess, and wherein said reduced diameter portion is externally threaded for a threaded engagement with an internally threaded proximal portion of the wall of said first coupling means defining said recess.

14. The intravascular lead of claim 9 wherein:
said electrode is porous and comprises said fluid passageway, and said recess is open to said electrode.

15. An intravascular, implantable lead including:
an electrode positionable for fixation to bodily tissue at a selected location; a flexible electrical conductor; a flexible, biocompatible, dielectric sheath surrounding said conductor substantially along the entire length thereof; a coupling means for electrically and mechanically joining said electrode and the distal end of said conductor; and
means forming a recess in said coupling means, means forming a passageway for admitting bodily fluid into and out of said recess, and a plurality of matrices contained in said recess, each matrix loaded with a water soluble drug, said matrices differing from one another in at least one of the following characteristics:
(a) the drug contained in the matrix;
(b) the concentration of the drug contained in the matrix; and
(c) the constituent material forming the matrix.

16. The intravascular lead of claim 15 wherein:
said recess is cylindrical and open to the distal end of said coupling means; and wherein said matrices are serially arranged and cylindrical, each matrix having an outside diameter substantially equal to the inside diameter of said recess.

17. The intravascular lead of claim 16 wherein:
said matrices contain the same drug, with the concentration of said drug in said matrices increasing sequentially from the most proximal to the most distal matrix.

18. The intravascular lead of claim 15 wherein:
said recess is cylindrical and open to the distal end of said coupling means, and wherein said matrices are serially arranged and toroidal, each matrix having an outside diameter substantially equal to the inside diameter of said recess.

19. The intravascular lead of claim 18 wherein:
the drug loaded into each of said matrices is uniformly distributed throughout its associated matrix.

20. The intravascular lead of claim 15 wherein:
said recess is cylindrical and open to the distal end of said coupling means, and wherein said matrices are toroidal, each matrix having an outside diameter less than the inside diameter of said recess.

21. The intravascular lead of claim 20 wherein:
first, second and third ones of said matrices contain an antibiotic, an anti-inflammation drug, and an anti-arrhythmic drug, respectively.

22. The intravascular lead of claim 15 wherein:
said recess is cylindrical and open to the distal end of said coupling means, and wherein said matrices are elongate and in side-by-side arrangement, with each matrix spanning substantially the length of said recess.

23. The intravascular lead of claim 15 wherein:
each of said matrices contains a different drug.

24. The intravascular lead of claim 15 wherein:
said recess is substantially cylindrical and open to the distal end of said coupling means, and wherein said matrices comprise elongate, concentric toroidal members spanning substantially the length of said recess.

25. An intravascular, implantable lead including:
an electrode positionable for fixation to bodily tissue at a selected location; a flexible electrical conductor; a flexible, biocompatible, dielectric sheath surrounding said conductor substantially along the entire length thereof; a coupling means for electrically and mechanically joining said electrode and the distal end of said conductor; and
means forming a recess in said coupling means, means forming a passageway for admitting bodily fluid into and out of said recess, and a toroidal matrix loaded with a water soluble drug and contained in said recess.

* * * * *